(12) United States Patent
Leisinger

(10) Patent No.: US 8,556,912 B2
(45) Date of Patent: Oct. 15, 2013

(54) TAPER DISENGAGEMENT TOOL

(75) Inventor: Steven R. Leisinger, Silver Lake, IN (US)

(73) Assignee: Depuy Synthes Products, LLC, Raynham, MA (US)

( * ) Notice: Subject to any disclaimer, the term of this patent is extended or adjusted under 35 U.S.C. 154(b) by 1544 days.

(21) Appl. No.: 11/927,811

(22) Filed: Oct. 30, 2007

(65) Prior Publication Data
US 2009/0112216 A1 Apr. 30, 2009

(51) Int. Cl.
A61B 17/58 (2006.01)
(52) U.S. Cl.
USPC .......................................................... 606/99
(58) Field of Classification Search
USPC ................................ 606/99, 105, 90; 29/256
See application file for complete search history.

(56) References Cited

U.S. PATENT DOCUMENTS

| | | | |
|---|---|---|---|
| 3,541,868 | A | 11/1970 | Hall |
| 3,749,365 | A | 7/1973 | Van Gompel |
| 3,810,312 | A | 5/1974 | Carson |
| 3,889,558 | A | 6/1975 | Duncan |
| 4,305,394 | A | 12/1981 | Bertuch, Jr. |
| 4,457,306 | A | 7/1984 | Borzone |
| 4,601,289 | A | 7/1986 | Chiarizzio |
| D290,399 | S | 6/1987 | Kitchens |
| 4,686,971 | A | 8/1987 | Harris et al. |
| 4,830,147 | A | 5/1989 | Kawada |
| 4,959,066 | A | 9/1990 | Dunn |
| 5,002,578 | A | 3/1991 | Luman |
| 5,002,581 | A | 3/1991 | Paxson |
| 5,016,858 | A | 5/1991 | Mitchell |
| 5,049,150 | A | 9/1991 | Cozad |
| 5,057,112 | A | 10/1991 | Sherman |
| 5,061,271 | A | 10/1991 | Van Zile |
| 5,190,550 | A | 3/1993 | Miller |
| D337,639 | S | 7/1993 | Beckman |
| 5,342,363 | A | 8/1994 | Richelsoph |
| 5,352,231 | A | 10/1994 | Brumfield |
| 5,405,404 | A | 4/1995 | Gardner |
| 5,409,492 | A | 4/1995 | Jones |
| 5,476,466 | A | 12/1995 | Barrette et al. |
| 5,540,687 | A | 7/1996 | Fairley |

(Continued)

FOREIGN PATENT DOCUMENTS

| | | |
|---|---|---|
| DE | 3023942 A1 | 1/1982 |
| DE | 10014401 A1 | 6/2001 |

(Continued)

OTHER PUBLICATIONS

Metasul LDH Large Diameter Head Surgical Technique, Enhancing Stability and Increasing Range of Motion—Zimmer.

(Continued)

*Primary Examiner* — Kevin T Truong
*Assistant Examiner* — Michael Araj

(57) ABSTRACT

A disassembly tool for disassembly of a first component of a prosthesis from a second component of the prosthesis for use in joint arthroplasty. The tool includes a body having an internal bore. At least a portion of the internal bore is threaded for engagement with a thread on the first component of the prosthesis. The tool further includes an expandable ring surrounding a portion of the body and adapted to engage the first component, such that when a radial force is applied to the body, the ring expands, applying an axial force against the first component.

6 Claims, 5 Drawing Sheets

(56) References Cited

U.S. PATENT DOCUMENTS

| | | | |
|---|---|---|---|
| 5,653,765 A | 8/1997 | McTighe | |
| 5,735,857 A | 4/1998 | Lane | |
| 5,849,015 A | 12/1998 | Haywood et al. | |
| 5,858,020 A | 1/1999 | Johnson | |
| 5,876,459 A | 3/1999 | Powell | |
| 5,938,701 A | 8/1999 | Hiernard | |
| 6,013,082 A | 1/2000 | Hiernard | |
| 6,063,123 A | 5/2000 | Burrows et al. | |
| 6,080,162 A | 6/2000 | Dye | |
| 6,110,179 A | 8/2000 | Flivik | |
| 6,165,177 A | 12/2000 | Wilson | |
| 6,187,012 B1 | 2/2001 | Masini | |
| 6,193,759 B1 | 2/2001 | Ro | |
| 6,238,435 B1 | 5/2001 | Meulink et al. | |
| 6,319,286 B1 | 11/2001 | Fernandez et al. | |
| 6,330,845 B1 | 12/2001 | Meulink | |
| 6,488,713 B1 | 12/2002 | Hershberger | |
| 6,491,696 B1 | 12/2002 | Kunkel | |
| 6,613,091 B1 | 9/2003 | Zdeblick | |
| 6,706,072 B2 | 3/2004 | Dwyer | |
| 6,712,825 B2 | 3/2004 | Aebi | |
| 6,743,235 B2 | 6/2004 | Subba Rao | |
| 6,755,841 B2 | 6/2004 | Fraser | |
| 6,840,944 B2 | 1/2005 | Suddaby | |
| 6,883,217 B2 * | 4/2005 | Barrette et al. | 29/256 |
| 6,905,515 B1 | 6/2005 | Gilbertson | |
| 6,911,048 B2 | 6/2005 | Fernandez et al. | |
| 7,022,141 B2 | 4/2006 | Dwyer | |
| 7,066,042 B2 | 6/2006 | Andrews | |
| 7,188,556 B1 | 3/2007 | Rinner | |
| 7,189,242 B2 | 3/2007 | Boyd | |
| 7,204,851 B2 | 4/2007 | Trieu | |
| 7,297,166 B2 | 11/2007 | Dwyer | |
| 7,363,838 B2 | 4/2008 | Abdelgany | |
| 7,387,635 B2 | 6/2008 | Keller | |
| 7,431,723 B2 | 10/2008 | Hazebrouck | |
| 7,582,092 B2 | 9/2009 | Jones | |
| 7,585,329 B2 | 9/2009 | McCleary | |
| 2002/0004684 A1 | 1/2002 | Thomas | |
| 2003/0149487 A1 | 8/2003 | Doubler | |
| 2003/0225417 A1 | 12/2003 | Fischell | |
| 2004/0010262 A1 | 1/2004 | Parkinson | |
| 2004/0054373 A1 | 3/2004 | Serra | |
| 2004/0073315 A1 | 4/2004 | Justin | |
| 2004/0111861 A1 | 6/2004 | Barrette | |
| 2004/0122437 A1 | 6/2004 | Dwyer | |
| 2004/0122439 A1 | 6/2004 | Dwyer | |
| 2004/0122440 A1 | 6/2004 | Daniels | |
| 2004/0122525 A1 | 6/2004 | Daniels | |
| 2004/0172139 A1 | 9/2004 | Dwyer | |
| 2004/0236342 A1 | 11/2004 | Ferree | |
| 2004/0260297 A1 * | 12/2004 | Padget et al. | 606/72 |
| 2004/0267267 A1 | 12/2004 | Daniels | |
| 2004/0267373 A1 | 12/2004 | Dwyer | |
| 2005/0033444 A1 | 2/2005 | Jones | |
| 2005/0085820 A1 * | 4/2005 | Collins et al. | 606/79 |
| 2005/0209597 A1 | 9/2005 | Long et al. | |
| 2005/0234559 A1 | 10/2005 | Fernandez et al. | |
| 2006/0027027 A1 | 2/2006 | Serra | |
| 2006/0058810 A1 | 3/2006 | Wozencroft et al. | |
| 2006/0217737 A1 | 9/2006 | Iversen | |
| 2006/0260440 A1 | 11/2006 | Abdelgany | |
| 2007/0005144 A1 | 1/2007 | Leisinger | |
| 2007/0123908 A1 | 5/2007 | Jones | |
| 2007/0260315 A1 | 11/2007 | Foley | |
| 2008/0077156 A1 | 3/2008 | Emstad | |
| 2008/0091212 A1 | 4/2008 | Dwyer | |
| 2008/0114367 A1 | 5/2008 | Meyer | |
| 2008/0275457 A1 | 11/2008 | Meek | |
| 2009/0112216 A1 | 4/2009 | Leisinger | |
| 2009/0112218 A1 | 4/2009 | McCleary | |
| 2009/0187251 A1 | 7/2009 | Justin | |
| 2009/0307887 A1 | 12/2009 | Jones | |

FOREIGN PATENT DOCUMENTS

| | | | |
|---|---|---|---|
| DE | 20114835 | U1 | 1/2002 |
| DE | 2006000845 | U1 | 5/2006 |
| EP | 333990 | A2 | 9/1989 |
| EP | 1000595 | A | 5/2000 |
| EP | 0728449 | B1 | 7/2002 |
| EP | 1435223 | A1 | 7/2004 |
| EP | 1522284 | A2 | 4/2005 |
| EP | 1191906 | B1 | 6/2005 |
| EP | 1738723 | A | 1/2007 |
| EP | 1905396 | A1 | 4/2008 |
| EP | 2055273 | A1 | 5/2009 |
| EP | 2057969 | A2 | 5/2009 |
| EP | 2057969 | B1 | 5/2011 |
| FR | 2606628 | A1 | 5/1988 |
| FR | 2926212 | A1 | 7/2009 |
| WO | WO 01/67997 | A1 | 9/2001 |
| WO | WO 2004089224 | A2 | 10/2004 |
| WO | WO 2007098549 | A1 | 9/2007 |

OTHER PUBLICATIONS

Zimmer, "Metasul LDH Large Diameter Head," Surgical Technique Enhancing Stability and Increasing Range of Motion, available at least as early as Sep. 28, 2006 (19 pages).

S-Rom Modular Hip System, Retrieved From Johnson & Johnson Gateway Web Site http://www.jnj.gateway.com/home.jhtml?loc=USENG&page=viewContent&contented=fc0de0010000030, retrieved on Sep. 26, 2005, 1 page.

Zimmer Fracture Equipment & Orthopaedic Appliances, 1 page, Published At Least As Early As Sep. 29, 2005.

* cited by examiner

TAPER DISENGAGEMENT TOOL

TECHNICAL FIELD OF THE INVENTION

The present invention relates generally to the field of orthopaedics, and more particularly, to an implant for use in arthroplasty.

BACKGROUND OF THE INVENTION

Patients who suffer from the pain and immobility caused by osteoarthritis and rheumatoid arthritis have an option of joint replacement surgery. Joint replacement surgery is quite common and enables many individuals to function properly when it would not be otherwise possible to do so. Artificial joints are usually comprised of metal, ceramic and/or plastic components that are fixed to existing bone.

Such joint replacement surgery is otherwise known as joint arthroplasty. Joint arthroplasty is a well-known surgical procedure by which a diseased and/or damaged joint is replaced with a prosthetic joint. In a typical total joint arthroplasty, the ends or distal portions of the bones adjacent to the joint are resected or a portion of the distal part of the bone is removed and the artificial joint is secured thereto.

There are known to exist many designs and methods for manufacturing implantable articles, such as bone prostheses. Such bone prostheses include components of artificial joints such as elbows, hips, knees and shoulders.

During performance of a joint replacement procedure, it is generally necessary to provide the surgeon with a certain degree of flexibility in the selection of a prosthesis. In particular, the anatomy of the bone into which the prosthesis is to be implanted may vary somewhat from patient to patient. Such variations may be due to, for example, the patient's age, size and gender. For example, in the case of a femoral prosthesis, the patient's femur may be relatively long or relatively short thereby requiring use of a femoral prosthesis, which includes a stem that is relatively long or short, respectively. Moreover, in certain cases, such as when use of a relatively long stem length is required, the stem must also be bowed in order to conform to the anatomy of the patient's femoral canal.

Such a need for prostheses of varying shapes and sizes thus creates a number of problems in regard to the use of a one-piece prosthesis. For example, a hospital or surgery center must maintain a relatively large inventory of prostheses in order to have the requisite mix of prostheses needed for certain situations, such as trauma situations and revision surgery. Moreover, since the bow of the stem must conform to the bow of the intramedullary canal of the patient's femur rotational positioning of the upper portion of the prosthesis is limited thereby rendering precise location of the upper portion and hence the head of the prosthesis very difficult. In addition, since corresponding bones of the left and right side of a patient's anatomy (e.g. left and right femur) may bow in opposite directions, it is necessary to provide (left) and (right) variations of the prosthesis in order to provide anteversion of the bone stem, thereby further increasing the inventory of prostheses which must be maintained.

As a result of these and other drawbacks, a number of modular prostheses have been designed. As its name implies, a modular prosthesis is constructed in modular form so that the individual elements or figures of the prosthesis can be selected to fit the needs of a given patient's anatomy. For example, modular prostheses have been designed which include a proximal neck component which can be assembled to any one of numerous distal stem components in order to create an assembly which fits the needs of a given patient's anatomy. Such a design allows the distal stem component to be selected and thereafter implanted in the patient's bone in a position which conforms to the patient's anatomy while also allowing for a limited degree of independent positioning of the proximal neck component relative to the patient's pelvis.

One issue that arises as a result of the use of a modular prosthesis is the locking of the components relative to one another. In particular, firm reproducible locking of the proximal neck component to the distal stem component is critical to prevent separation of the two components subsequent to implantation thereof into the patient. The need for the firm locking is particularly necessary if the design does not provide for positive locking with weight bearing. As such, a number of locking mechanisms have heretofore been designed to lock the components of a modular prosthesis to one another. For example, a number of modular prostheses have heretofore been designed to include a distal stem component, which has an upwardly extending post, which is received into a bore defined distal neck component. A relatively long fastener such as a screw or bolt is utilized to secure the post with the bore. Other methods of securing modular components include the impacting of one component onto the other. This method has highly variable results.

Current designs of modular stems include designs in which the modular connection utilizes a tapered fit between the two components. For example, the proximal body may include an internal taper, which mates with an external taper on the distal stem. Such a taper connection may be used in conjunction with additional securing means, for example, a threaded connection or may be used alone. It is important that the tapered connection be secure. For example, the proper amount of force must be applied to the tapered connection to properly secure the tapered connection so that the connection can withstand the forces associated with the operation of the stem.

In certain instances, it may be desired to disassociate the two components. For example, after the surgery, if there are problems with the implant, the surgeon may need to do a revision that would require removing the original proximal body from the stem. Other times, the surgeon may discover after assembling the proximal body and the stem that a different sized stem or body would be more appropriate. In such instances, the surgeon would have to disassemble the stem from the body. In these cases, removing the proximal body from the stem can be very difficult. Because the tapered connection is so secure, it requires a great amount of force to disassociate the components. In some designs, the surgeon may have to apply 2000 pounds of axial force in order to separate the components.

There are currently some disengagement tools in use for disassociating the proximal body from the distal stem. However, these devices have proven to be unsuccessful. Some of the current devices may even break the components.

Therefore, there is a need for a tool that allows a surgeon to easily and safely disengage the taper lock between the proximal body and the distal stem.

SUMMARY OF THE INVENTION

According to one embodiment of the present invention, a disassembly tool for disassembly of a first component of a prosthesis from a second component of the prosthesis for use in joint arthroplasty is provided. The tool includes a body having an internal bore. At least a portion of the internal bore is threaded for engagement with a thread on the first component of the prosthesis. The tool also includes an expandable ring surrounding a portion of the body and adapted to engage the first component, such that when a radial force is applied to the body, the ring expands, applying an axial force against the first component.

According to another embodiment of the present invention, a method of disassembling a first and second component of a prosthesis used in joint arthroplasty is provided. The method includes providing a first component having a male taper and a second component having an internal bore with a female taper. The first component and second component are engaged via the male and female tapers. A disassembly tool is inserted into the inner bore of the second component. The disassembly tool has a body and an expandable portion. The body is coupled to the first component. Through a frictional force the expandable portion and an inner diameter of the second component become engaged. The threaded internal bore of the disassembly tool is partially dethreaded from the first component. The expandable portion and the inner diameter of the second component expand, disengaging the first component from the second component.

According to yet another embodiment of the present invention, a kit is provided. The kit includes a first component having a male taper and a second component having an internal bore with a female taper. The first component and second component are engageable via the male and female tapers. The kit also includes a disassembly tool having a body and an expandable portion separable from the body, such that the expandable portion has an initial outer diameter equal to the inner diameter of the internal bore of the second component.

Other technical advantages of the present invention will be readily apparent to one skilled in the art from the following figures, descriptions and claims.

BRIEF DESCRIPTION OF THE DRAWINGS

For a more complete understanding of the present invention and the advantages thereof, reference is now made to the following description taken in connection with the accompanying drawings, in which.

DETAILED DESCRIPTION OF THE INVENTION

Embodiments of the present invention and the advantages thereof are best understood by referring to the following descriptions and drawings, wherein like numerals are used for like and corresponding parts of the drawings.

Figure 1:
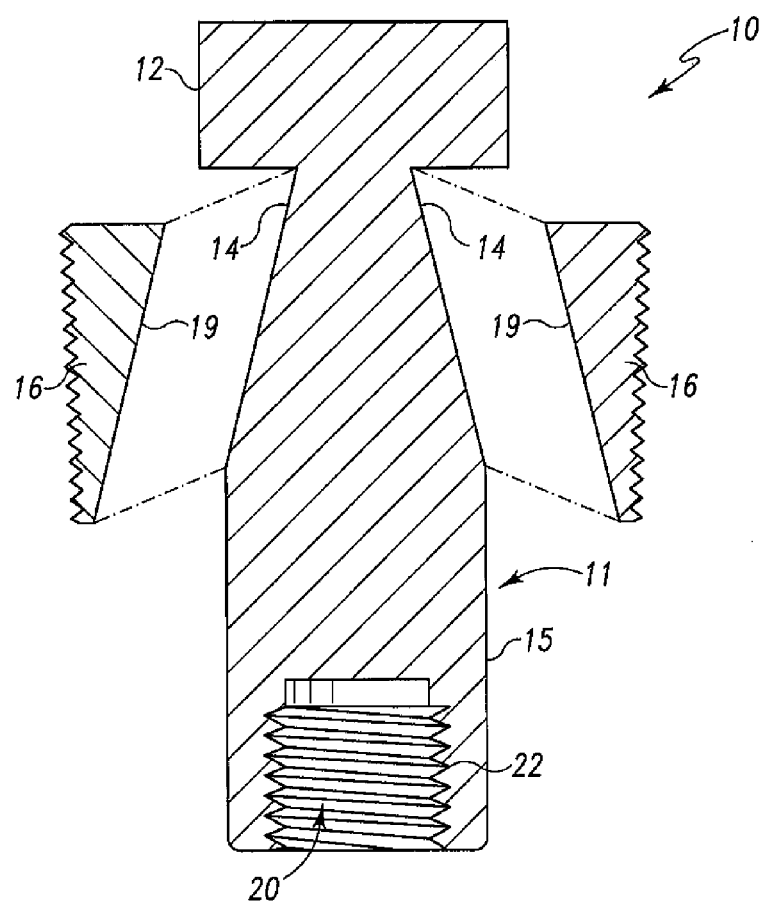
FIG. 1 is a perspective view of a disengagement tool according to one embodiment of the present invention.
Figure 2:
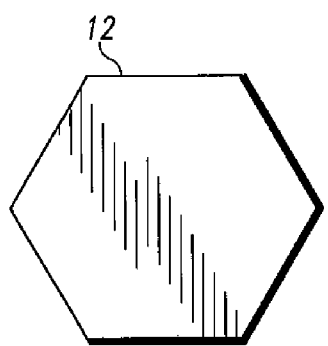
FIG. 2 is a top view of the disengagement tool of FIG. 1.
Figure 3:
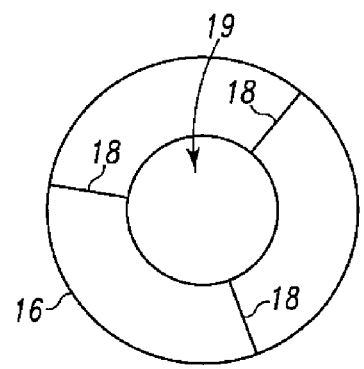
FIG. 3 is a plan view of a two-pieced modular hip stem that may be disassembled with the disassembly tool of FIG. 1.

Referring now to FIG. 1, a disassembly tool 10 according to one embodiment of the present invention is illustrated. The disassembly tool 10 includes a body 11 having a top portion 12, a tapered portion 14, and a bottom portion 15. The tool 10 also includes a ring portion 16 (FIG. 3). As illustrated in the top view of FIG. 2, the top portion 12 is hex-shaped. The hex-shape of the top portion 12 allows the top portion to be grasped by common tools.

Turning back to FIGS. 1 and 3, as shown, the ring 16 is generally cylindrical and includes a plurality of perforations 18. The perforations 18 allow the ring 16 to break into pieces when a force is applied against the ring 16. The ability to break into pieces allows the ring 16 to be inserted into a space that has a greater diameter than the outer diameter of the ring 16. However, if a force is applied that causes the ring 16 to break into pieces, the effective outer diameter of the ring 16 enlarges. As illustrated in FIG. 3, the ring 16 includes an inner bore 19. The bore 19 is tapered in the embodiment illustrated in FIG. 1, but may be non-tapered in other embodiments.

The body 11 also includes an internal bore 20. The internal bore 20 in the embodiment shown in FIG. 1 extends through part of the bottom portion 15. In other embodiments, the bore 20 may extend through the entire body 11. In the embodiment illustrated in FIG. 1, the internal bore 20 includes a threaded portion 22 that extends along the length of the bore 20. In some embodiments, the threaded portion includes clockwise threads—meaning that the threads are designed to engage other threads when rotated in a clockwise fashion and to disengage other threads when rotated in a counter-clockwise fashion.

Figure 4:
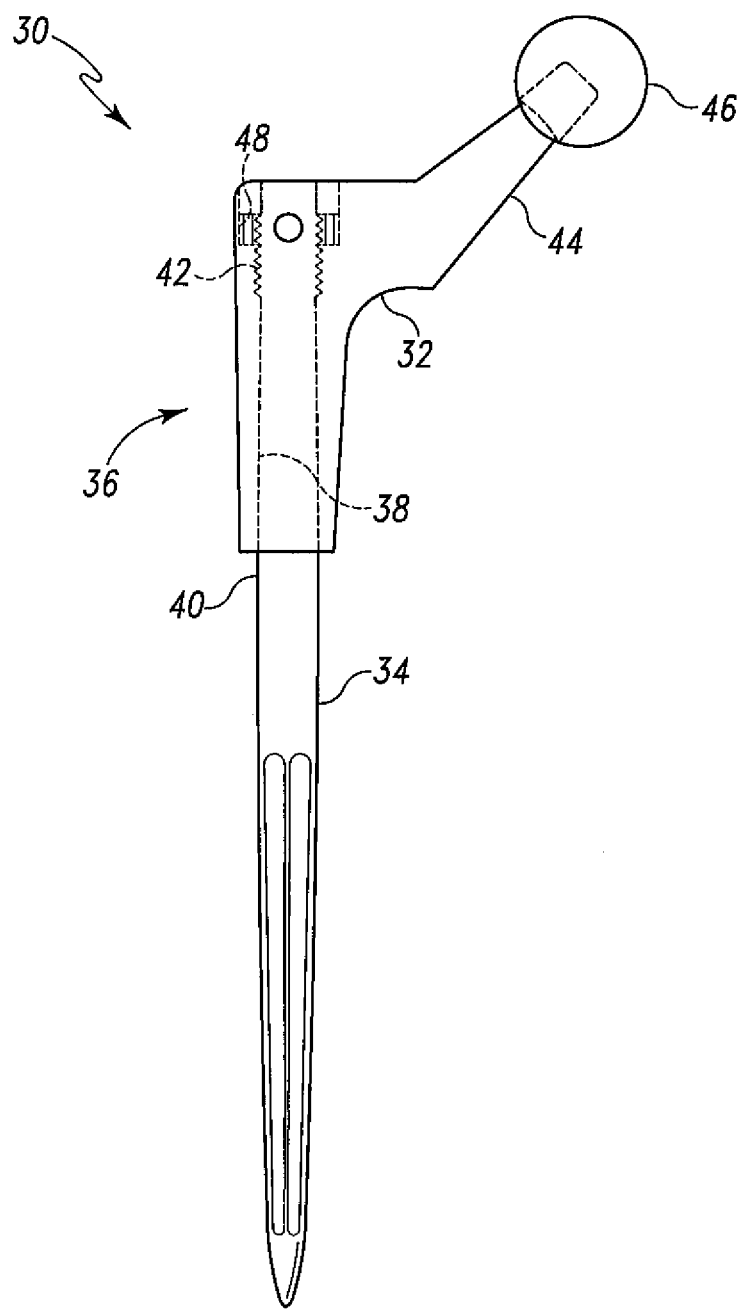
FIG. 4 is a plan view of the modular hip stem of FIG. 3.

Turning now to FIG. 4, a prosthesis 30 is shown in greater detail. The prosthesis 30 as shown in FIG. 4 includes a proximal body 32 and a distal stem 34, which have an interference connection that is, for example, an interference connection of a cylindrical bore to a cylindrical stem, as well as, a splined non-uniform cross-section stem to a splined or non-uniform cross-section opening. It should further be appreciated that the proximal body and distal stem of the prosthesis 30 for use with the assembly tool of the present invention may include a taper connection 36 in which the distal stem 34 has an internal taper 38 and the proximal body 32 has an external taper 40. The taper connection 36 consists of an external taper 40 formed on the distal stem 34 that engages with internal taper 38 formed on the proximal body 32.

The prosthesis 30 as shown may include external threads 42 formed on the distal stem 34. The proximal body 32 may include a neck 44 to which a head 46 may matingly be fitted. As an additional precaution in assuring that the proximal body 32 remains secured to the distal stem 34, the prosthesis 30 may further include a nut 48 which threadably engages the external threads 42 of the distal stem 34.

Figure 5:
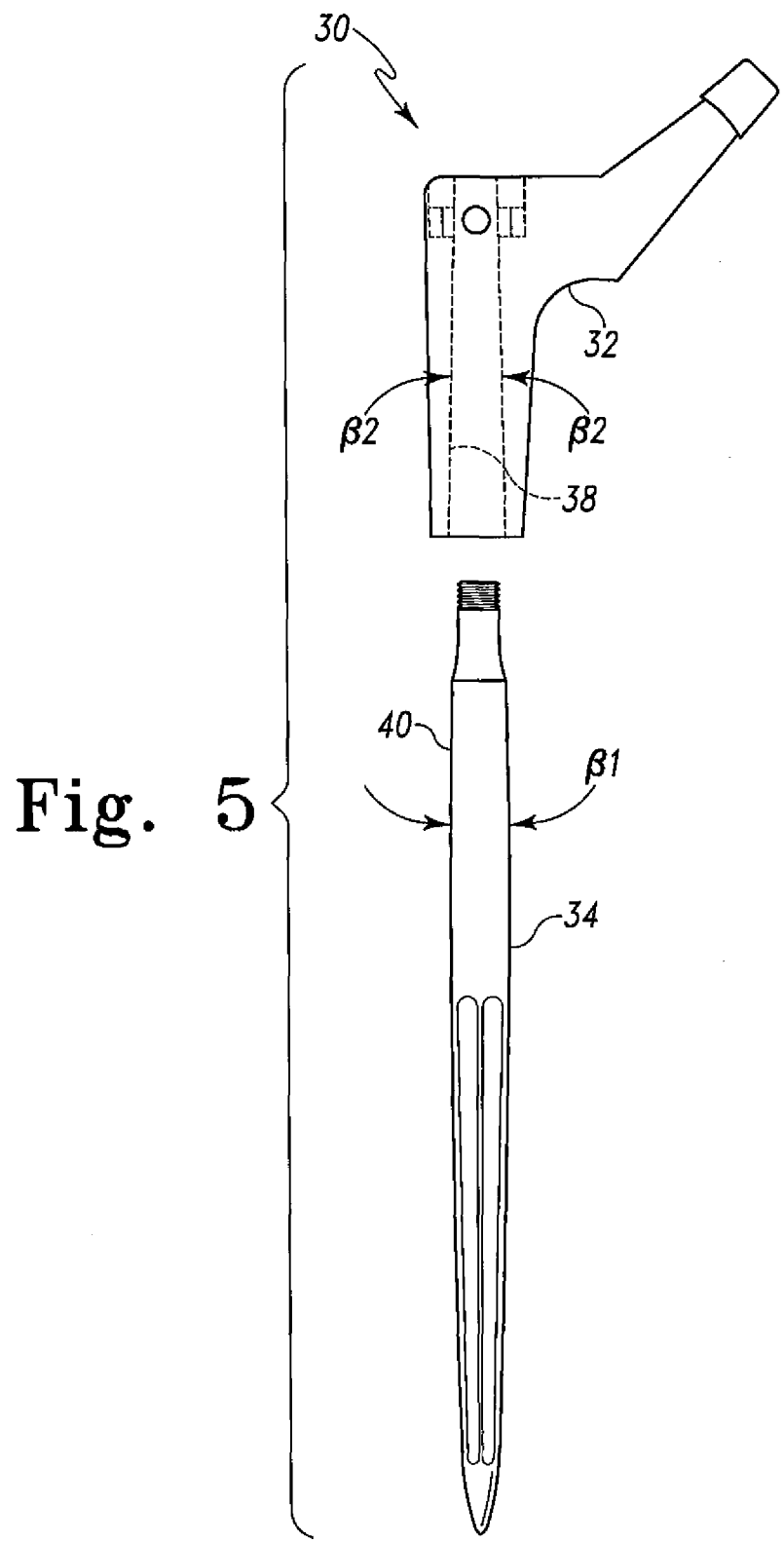
FIG. 5 is an expanded view of the modular hip system of FIG. 3.

Referring now to FIG. 5, the prosthesis 30 is shown with the proximal body 32 disassembled from the distal stem 34. The external taper 40 of the distal stem 34 is defined by an included angle $\beta 1$. In order that the proximal body 32 fits securely to the distal stem 34, the proximal body 32 includes the internal taper 38 defined by included angle $\beta 2$. The angles $\beta 1$ and $\beta 2$ may be generally the same. Alternatively the taper angle may be divergent. The angles $\beta 1$ and $\beta 2$ should be chosen, such that the fit of the proximal body 32 to the distal stem 34 is secure.

As discussed previously in the background section, in some instances, the internal and external tapers 38, 40 lock the proximal body 32 to the distal stem 34. This can be problematic should the surgeon need to disengage the proximal body 32 from the distal stem 34.

Figure 6:
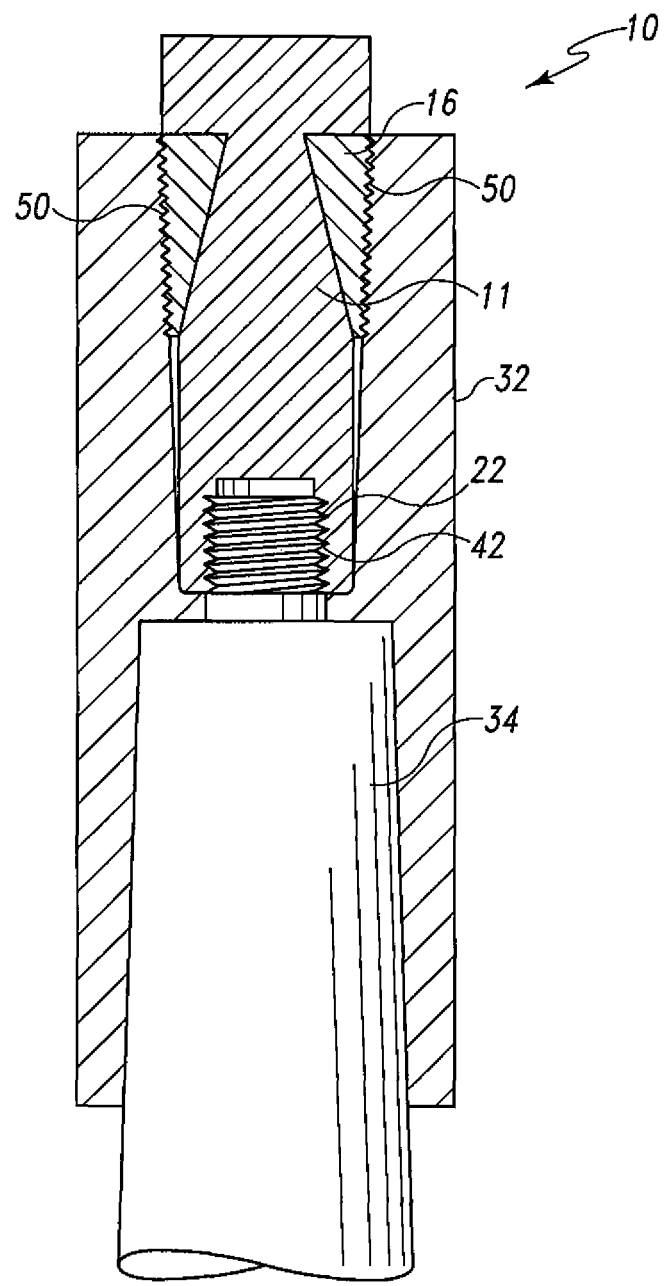
FIG. 6 is a cross-sectional view of a disengagement tool according to one embodiment of the present invention.

Turning now to FIG. 6, the tool 10 is shown inserted into the proximal body 32 and distal stem 34. As shown, the threads 22 of the tool 10 engage the threads 42 of the distal stem 34. The ring 16 is shown in place between the proximal body 32 and the body 11 of the tool 10. The ring 16 may include serrated edges 50 to allow the ring 16 to grasp the inner diameter of the proximal body 32.

Figure 7:
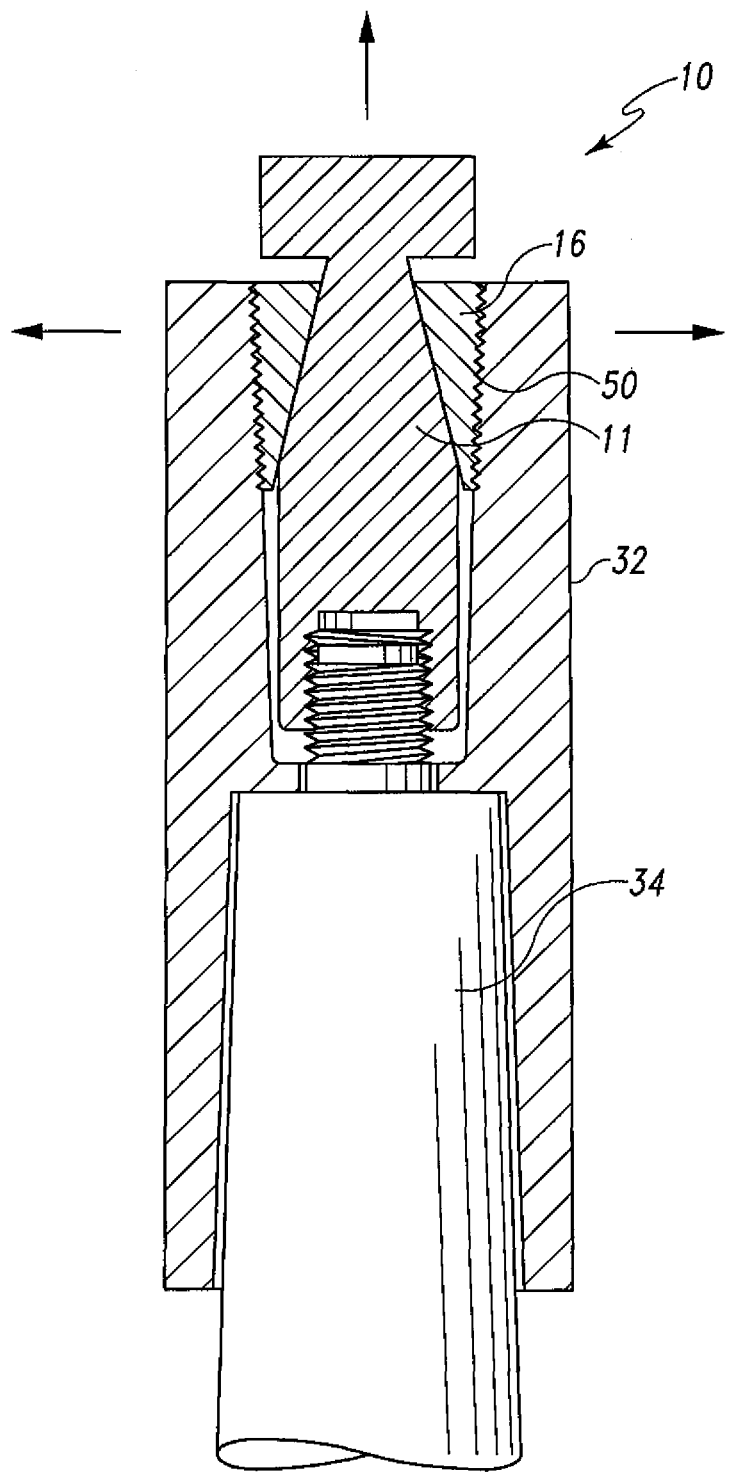
FIG. 7 is a cross-sectional view of a disengagement tool inserted into an implant according to one embodiment of the present invention.

As shown in FIG. 7, when the user turns the body 11 counterclockwise, the threads 22 disengage from the threads 42 of the distal stem and the body 11 moves upward relative to the proximal body 32 and distal stem 34. Because of the serrated edges 50 of the ring 16 grasp the inner diameter of the proximal body 32, the ring 16 does not advance with the body 11. Instead, as the body 11 exerts a radial force against the ring 16, the perforations 18 (FIG. 3) break, creating three ring pieces that push against the inner diameter of the proximal body 32. As the body 11 turns, the radial force applied to the body translates into an axial force against the inner diameter of the proximal body 32, thereby breaking the taper lock, and allowing the proximal body 32 to be removed from the stem 34.

Therefore, breaking the lock does not require pulling the taper off-center or using a great amount of force. Merely by utilizing a common wrench, the taper lock can be broken.

In other embodiments, the ring 16 may be broken apart by the insertion of a sleeve (not shown). The sleeve would have a diameter greater than the ring 16 and would force the ring 16 to break into pieces. In yet other embodiments, the ring 16 could include a groove with an elastomer band. As the body 11 is pulled away from the proximal body 32, the elastomer band would keep the ring 16 in place. The user could then use a hollow tube or an impact to disengage the ring 16 from the body 11. Alternatively, some sort of adhesive could be used to keep the ring 16 in place during insertion into the proximal body 32.

In the illustrated embodiment, the bore 19 is tapered at an angle that matches the tapered portion 14 of the body 11. However, in other embodiments, the bore 19 may not be tapered or may be tapered at a different angle.

In the illustrated embodiment the outside of the ring 16 is angled the same as the inside of the proximal body 32. However, in other embodiments, the outside of the ring 16 may have an angle that is different than that of the proximal body 32.

Although the present invention and its advantages have been described in detail, it should be understood that various changes, substitutions, and alterations can be made therein without departing from the spirit and scope of the present invention as defined by the appended claims.

I claim:

1. A disassembly tool for disassembly of a first component of a prosthesis from a second component of the prosthesis for use in joint arthroplasty, the tool comprising:
   a body having an internal bore at one end, at least a portion of the internal bore being threaded for engagement with a thread on the first component of the prosthesis, and being tapered inwardly towards its opposite end; and
   an expandable ring surrounding the tapered portion of the body, the ring having a tapered internal bore so that, when the tapered portion of the body is moved within the bore, radial force is applied to the ring which causes it to expand radially to engage the second component, allowing an axial force to be applied through the body against the first component relative to the second component.

2. The tool according to claim 1, wherein the expandable ring includes at least one perforation, such that when a force is applied, the expandable ring breaks into at least two pieces.

3. The tool according to claim 1, wherein the body has a generally hex-shaped head at the end which is opposite to the end which has the internal threaded bore.

4. The tool according to claim 3, wherein the taper on the internal bore in the ring matches the taper on the tapered portion of the body.

5. The tool according to claim 3, wherein the expandable ring has outwardly facing edges which are serrated to promote engagement between it and the second component.

6. The tool according to claim 3, wherein the bottom portion of the body includes a threaded bore.

* * * * *